United States Patent [19]

Chu et al.

[11] Patent Number: 4,719,004

[45] Date of Patent: Jan. 12, 1988

[54] CRACKING/DEWAXING WITH HIGH SILICA ZEOLITE MULLED WITH WATER AND BINDER

[75] Inventors: Pochen Chu, West Deptford; William E. Garwood, Haddonfield, both of N.J.

[73] Assignee: Mobil Oil Corporation, New York, N.Y.

[21] Appl. No.: 920,015

[22] Filed: Oct. 17, 1986

Related U.S. Application Data

[63] Continuation-in-part of Ser. No. 792,349, Oct. 29, 1985, abandoned, which is a continuation-in-part of Ser. No. 620,365, Jun. 13, 1984, Pat. No. 4,563,435, which is a continuation-in-part of Ser. No. 391,212, Jun. 23, 1982, abandoned.

[51] Int. Cl.$^4$ .................... C10G 11/05; C10G 45/64; C10G 47/20
[52] U.S. Cl. .................................. 208/111; 208/120
[58] Field of Search ............... 208/111, 120, 110, 118, 208/119

[56] References Cited

U.S. PATENT DOCUMENTS 4,247,388 1/1981 Banta et al. ...................... 208/111
4,441,991 4/1984 Dwyer et al. ..................... 208/111

Primary Examiner—Olik Chaudhuri
Attorney, Agent, or Firm—Alexander J. McKillop; Michael G. Gilman; Dennis P. Santini

[57] ABSTRACT

A cracking/dewaxing process is provided with a catalyst composition prepared by the steps of (1) mulling, in the presence of water, a crystalline zeolite having less than about 1000 ppm alumina and an Alpha Value of less than about 5 with an inorganic binder, (2) forming the composition of step (1) at a pressure of from 2 to about 50 tons per square inch, (3) calcining the formed composition of step (2), (4) base exchanging the calcined composition of step (3) if it has a sodium content greater than about 0.02 wt. % in order to reduce the sodium content to less than 0.02 wt. %, and (5) calcining the product of step (4). In a particular embodiment wherein the zeolite has a ZSM-5 type structure, the cracking is selective for waxes and the process is useful for reducing the pour point of fuel oils and lubricants.

17 Claims, No Drawings

CRACKING/DEWAXING WITH HIGH SILICA ZEOLITE MULLED WITH WATER AND BINDER

CROSS-REFERENCE TO RELATED APPLICATION

This is a continuation-in-part of application Ser. No. 792,349 filed Oct. 29, 1985, abandoned, which is a continuaton-in-part of application Ser. No. 620,365, filed June 13, 1984 now U.S. Pat. No. 563,435, which is a continuation-in-part of application Ser. No. 391,212, filed June 23, 1982, abandoned.

BACKGROUND OF THE INVENTION

1. Field of the Invention

This invention relates to use of crystalline silicates having a high silica/alumina mole ratio. In one aspect of this invention a novel catalytic composition is prepared from said high silica materials by reacting the same with certain binders such as an alumina-containing binder and in another aspect of this invention conversion processes, e.g. cracking and dewaxing, are carried out with said novel catalytic composition.

2. Description Of The Prior Art

High silica/alumina mole ratio crystalline silicates are well known in the art and it is generally accepted that the ion exchange capacity of such crystalline silicates is directly dependent on the amount of metal which is tetrahedrally coordinated with the silica in the framework. Thus, for example, with regard to the most common zeolitic crystalline materials; namely, crystalline aluminosilicate zeolites, such material can be described as a rigid three dimensional network of $SiO_4$ and $AlO_4$ in which the tetrahedra are cross-linked by the sharing of oxygen atoms whereby the ratio of total aluminum and silicon atoms to oxygen is 1:2. The electrovalence of the tetrahedra-containing aluminum is balanced by the inclusion in the crystal of a cation. Quite obviously, the more aluminum that is present in the crystal the more cations can be introduced into the crystalline structure. Recently, the scientific and technical literature has disclosed high silica-containing zeolitic structures wherein substantially all or a portion of the aluminum present in the crystal framework has been replaced by other metals either partially or completely. Thus, for example, iron, chromium and boron are materials which have been described in the prior art as capable of being substituted for aluminum in the crystal framework and quite obviously, the ion exchange capacity of the resulting zeolitic structure will again be determined by the amount of metal which is in tetrahedral coordination with the silica. Thus, for example, the more boron there is in a crystalline structure, the more cations are required to balance the electronegativity thereof and when such cations are of the acidic type, such as hydrogen, they impart tremendous catalytic activity to the crystalline material. On the other hand, crystalline silicates having a high silica/alumina mole ratio of greater than about 1600 have many important properties and characterisitcs and have a high degree of structural stability such that they have become candidates for use in various processes, incuding catalytic processes. Materials of this type are well known in the art and include high silica-containing aluminosilicates such as ZSM-5 (U.S. Pat. No. 3,702,886), ZSM-11 (U.S. Pat. No. 3,709,979), and ZSM-12 (U.S. Pat. No. 3,832,449) to mention a few. It is also known in the art that the silica/alumina ratio of a given zeolite is often variable. For example, zeolite X can be synthesized with a silica/alumina ratio of from 2 to 3 and zeolite Y from about 3 to about 6. In some zeolites, the upper limit of silica/alumina ratio is virtually unbounded. Zeolite ZSM-5 is one such material wherein the silica/alumina ratio is at least 5. U.S. Pat. No. 3,941,871 discloses a crystalline metallo-aluminosilicate essentially free of aluminum and exhibiting an X-ray diffraction pattern characteristic of ZSM-5. U.S. Pat. Nos. 4,061,724; 4,073,865; and 4,104,294 describe microporous crystalline silicas wherein the aluminum content is present at very low levels. Because of the extremely low aluminum content of these high silica-containing zeolites their ion exchange capacity is not as great as materials with a higher aluminum content. Therefore, when these materials are contacted with an acidic solution and thereafter are processed in a conventional manner, they are not as catalytically active as their higher aluminum containing counterparts. This invention permits the preparation and use of certain high silica-containing materials which have all the desirable properties inherently possessed by such high silica materials and yet have an acid activity which has heretofore only been possible to be achieved by materials having a higher aluminum content in their "as synthesized" form or by certain activation techniques, such as treatment with metallic vapors.

SUMMARY OF THE INVENTION

The present invention relates to use of a high silica crystalline material having improved acid activity such as, for example, catalytic cracking and dewaxing activity, as a result of reaction of said high silica material with an acidic inorganic oxide, e.g. alumina. The reaction requires mixing said high silica material with an acidic inorganic oxide in the presence of water, forming or shaping the mixture into a desired shape, and then calcining the formed or shaped mixture at an elevated temperature.

It has been found that it is absolutely crucial in this invention that the inorganic oxide, e.g. alumina, and the crystalline high silica material be physically admixed in the presence of water. If the materials are added in a completely dry state, absolutely no activation takes place irrespective of whether or not the later processing steps are carried out. In a particular preferred embodiment of this invention, the high silica zeolite and alumina are extruded under hydraulic pressures ranging from about 2 to about 50 tons per square inch ($t/in^2$). For reasons which are not completely understood, it has been found that the extrusion step under high pressure imparts even a greater activation to the high silica zeolitic material.

EMBODIMENTS

The present invention provides a process for converting a feedstock comprising hydrocarbon compounds to conversion product comprising hydrocarbon compounds of lower molecular weight than feedstock hydrocarbon compounds which comprises contacting said feedstock at conversion conditions sufficient to convert said feedstock to said product with a catalyst composition prepared by the method detailed herein.

In a specific embodiment, the present invention provides a process for catalytically dewaxing a heavy oil stock to provide a catalytically dewaxed oil with reduced wax content which comprises contacting said oil stock at catalytic dewaxing conditions in a reaction zone in the presence of hydrogen with a catalyst composition as herein defined.

In another specific embodiment, the present invention provides a process for catalytically hydrodewaxing a lubricating oil base stock to provide a catalytically hydrodewaxed lubricating oil base stock with reduced wax content which comprises contacting said stock at catalytic hydrodewaxing conditions in a reaction zone operating under a hydrogen partial pressure with a catalyst composition as herein defined.

This invention is concerned with use of high silica-containing crystalline materials. The expression "high silica-containing crystalline material" is intended to define a crystalline structure which has a silica/alumina mole ratio greater than about 1600 up to and including those highly siliceous material where the silica/alumina mole ratio is infinity, or as reasonably close to infinity as practically possible. This latter group of highly siliceous materials is exemplified by U.S. Pat. Nos. 3,941,871; 4,061,724; 4,073,865 and 4,104,294 wherein the materials are prepared from reaction solutions which involve no deliberate addition of aluminum. However, trace quantities of aluminum are usually present due to the impurity of the reaction solutions. It is to be understood that the expression "high silica-containing crystalline material" also specifically includes those materials which have other metals besides aluminum associated therewith, such as boron, iron, chromium, etc. Thus, the only requirements with regard to the starting materials utilized in the novel process of this invention is that they have a silica/alumina ratio greater than about 1600 (irrespective of what other materials or metals are present in the crystal structure).

As is well known in the art, the concept of incorporating a crystalline silicate including crystalline aluminosilicate zeolites with an inorganic oxide such as alumina, silica, titania, silica-alumina, etc. is well known in the art and these materials are broadly referred to as binders or matrices. The binders and matrices serve very valuable functions, including imparting extra strength to the zeolitic catalysts, but strictly from a catalytic point of view they are not as catalytically active as the zeolite with which they are admixed so that the total effect is that the catalytic activity of the composition has been reduced. Thus, it is conventional in the prior art to use an inorganic oxide binder such as alumina with a zeolite such as ZSM-5 but the resulting composition has less catalytic activity than would be obtainable by the use of the pure zeolite alone. Thus, quite simply put, the instant invention is not concerned with those crystalline silicates which have an inherently sufficiently high acid activity such that incorporating them with alumina would result in obtaining a composition which had less activity than the silicate material itself. This invention is concerned with crystalline silicate materials which have substantially little or no acid catalytic activity as conveniently measured by the Alpha test. They have Alpha Values of less than about 5. This invention would reside in improving said acid catalytic activity.

Another way of expressing the same concept is to point out that in one embodiment, the novel process of this invention involves the following steps: (1) mixing, such as by mulling, of a high silica zeolite with an inorganic oxide, such as alumina, and water, (2) forming or shaping, and (3) air calcining (e.g. in air) at elevated temperatures.

Optionally, the formed or shaped composition of step (2) is calcined in a non-oxidizing atmosphere, e.g. ammonia, at from about 900° F. to about 1200° F. for at least about one hour, preferably for from about one hour to about five hours. Also optionally, the formed or shaped composition of step (2) or the product of calcination thereof in a non-oxidizing atmosphere is treated with acidic cations, especially if the sodium content of the material is greater than about 0.02 wt. %, in order to insure less than 0.02 wt. % sodium content.

In short, the following list of steps will be followed by the present method:

(1) mixing with inorganic oxide in pressure of water
(2) forming or shaping,
(3) optionally calcining the formed or shaped composition in a non-oxidizing atmosphere,
(4) optionally treating with acidic cations if the sodium content of the material is greater than about 0.02 wt. %, and if treated,
(5) calcining the treated product.

It appears obvious that for certain zeolites, steps (3), (4), and (5) will result in enhancing their catalytic activity without carrying out steps (1) and (2). Thus, it is very well known in the art that base exchange of the sodium in a crystalline zeolite with acidic ions, such as ammonium ions, results in enhancing the acid activity of such material. As indicated earlier, this is because those materials contain sufficient aluminum in the framework structure such that they must be balanced by cations and base exchange with acidic ions allows the incorporation of a substantial amount of acidic cations into the crystal structure, thereby resulting in enhanced acid activity.

Clearly, if the steps (1) and (2) were carried out with a crystalline material having these characteristics no enhancement in acitivy would result, but rather, a dilution of activity would result merely because the inorganic oxide would dilute the acid activity of the far more active zeolitic component.

As indicated earlier, the high silica crystalline materials with which this invention is concerned contain very small amounts of aluminum, with or without iron, chromium, boron, etc. It is difficult to set exact numerical limits for the amount of such materials which the composition must contain n order to be operable within the novel process of this invention due to the fact that at such low levels analytical techniques are not necessarily accurate. However, in order to give some indication of the ranges of such content, it would be generally from about 50 to no more than about 1000 ppm, preferably no more than about 500 ppm, i.e. a silica/alumina mole ratio of greater than about 1600.

As has previously been indicated, the novel method for the preparation of catalysts having enhanced acid activity according to this invention involves carrying out at least three necessary steps. The first necessary step in the novel process of this invention involves (1) mixing, such as for example mulling, a crystalline silicate having a high silica/alumina mole ratio of greater than about 1600 and an Alpha Value of less than about 5 with an appropriate acidic inorganic oxide in the presence of water. It is absolutely crucial that there be water present during step (1) since it has been found that if the zeolite and the inorganic oxide material is mixed, e.g. mulled, in a dry state that substantially no activation will occur. The amount of water which is utilized is not narrowly critical and only enough water has to be used to ensure an adequate mixture of the inorganic oxide and the high silica material. The mixing can be carried out by hand with a mortar and pestle or commercially available mullers can be used. An example of such mullers are those manufacured by the Cincinnati Muller Company of Cincinnati, Ohio.

The acidic inorganic binder which is used in step (1) is preferably alumina or an alumina-containing material. However, other binders can be used such as titania and zirconia or mixtures of alumina, titania and zirconia. For reasons which are not completely understood, silica has essentially no effect on the acid activity of the material and, thus, cannot be used by itself.

The amount of inorganic oxide which is incorporated with the high silica crystalline material has a surprising effect on the acid activity of the resulting composition. The preferred range of inorganic oxide is, thus, 20–95 wt. % based on total composition of inorganic oxide plus high silica crystalline material.

The second necessary step in the novel process of this invention involves a forming step (2) so as to obtain discrete particles of the catalyst composite. The forming step includes simply sizing the material to any appropriate size using any appropriate die or compacting type device, including hand pelleting. The forming step also includes spray drying the step (1) mixture or using the oil-drop method. However, a preferred embodiment of this step is to use extrusion, i.e. to pass the composition of step (1) through a die at extremely high pressures, i.e. at pressures ranging from about 2 to about 50 t/in$^2$ or even higher, preferably higher than about 5 t/in$^2$. Typical extruders can be of the hydraulic ram type or of the bonnet auger type.

The third necessary step in the novel process of this invention involves calcination, such as in air, at elevated temperature, i.e. temperature from about 800°–1500° F. for periods of time ranging from about 2–5 hours. A particularly preferred embodiment would be air calcination at about 1000° F. for about three hours.

An optional step in the novel process of this invention involves calcination of the step (2) product in a non-oxidizing atmosphere at temperatures from about 900°–1200° F. for at least about 1 hour, e.g. 1–5 hours. The non-oxidizing atmosphere is preferably ammonia, although nitrogen and/or inert gases can be used.

A further optional step involves ion exchange of the composition with hydrogen ions or ammonium ions in order to reduce the sodium content to less than about 0.02 wt. %.

Of the high silica materials advantageously treated in accordance herewith, those having the structure of zeolite ZSM-5, ZSM-5/ZSM-11 intermediate or ZSM-11 are particularly noted. ZSM-5 is described in U.S. Pat. No. 3,702,886 and Reissue 29,948, the entire contents of each being incorporated herein by reference. ZSM-11 is described in U.S. Pat. No. 3,709,979, the teaching of which is hereby incorporated by reference. ZSM-5/ZSM-11 intermediate is described in U.S. Pat. No. 4,229,424, the entire contents thereof being incorporated herein by reference. Quite obviously, these materials must be used in the manner previously indicated, i.e. having a silica/alumina mole ratio of greater than about 1600 and an Alpha Value of less than about 5.

In general, organic compounds such as, for example, those selected from the group consisting of hydrocarbons are converted to conversion products such as, for example, lower molecular weight hydrocarbons, by way of the present process by contact under organic compound conversion conditions including a temperature of from about 100° C. to about 800° C., a pressure of from about 0.1 atmosphere (bar) to about 200 atmospheres, a weight hourly space velocity of from about 0.08 hr$^{-1}$ to about 2000 hr$^{-1}$ or a liquid hourly space velocity of from about 0.5 hr$^{-1}$ to about 100 hr$^{-1}$, and a hydrogen/feedstock organic e.g. hydrocarbon, compound mole ratio of from 0 (no added hydrogen) to about 100.

Such conversion processes include, as a non-limiting example, cracking hydrocarbons to lower molecular weight hydrocarbons with reaction conditions preferably including a temperature of from about 230° C. to about 800° C., a pressure of from about 0.1 atmosphere (bar) to about 35 atmospheres and a weight hourly space velocity of from about 0.1 hr$^{-1}$ to about 200 hr$^{-1}$, or a liquid hourly space velocity of from about 0.6 hr$^{-1}$ to about 10 hr$^{-1}$.

When the feedstock to the present process comprises a heavy oil stock to be dewaxed, preferred conversion temperature is from about 230° C. to about 500° C. When the feedstock comprises a lubricating oil base stock to be dewaxed, preferred conversion temperature is also from about 230° C. to about 500° C.

The following examples will illustrate the best mode contemplated for carrying out this invention.

EXAMPLE 1

Preparation of ZSM-5 containing about 50 ppm alumina (about 38,000:1 silica-to-alumina ratio)

ZSM-5 crystals were synthesized from a formulation containing tetraethylorthosilicate, sodium hydroxide, tetrapropylammonium bromide, and water at 212° F. with intensive agitation. Special precautions were taken to prevent alumina contamination from the crystallization equipment and the environment.

A 50 g quantity of the material was calcined in an ammonia atmosphere at 1000° F. for three hours to decompose the organic components in the zeolite. The product was pure white without any signs of a carbon residue. The NH$_3$ calcined material was subsequently purged with nitrogen and then air for one hour to remove any absorbed NH$_3$ The sodium content of the sample was reduced to 0.01 wt. % by treatment with a 0.1N ammonium nitrate solution followed by hot water washing. The sample was then dried and its chemical composition was determined to be as follows:

| | |
|---|---|
| Al$_2$O$_3$, ppm | 50 |
| SiO$_2$, wt. % | >99 |
| Na, wt. % | 0.01 |
| N, wt. % | <0.05 |
| C, wt. % | <0.03 |
| Ash, wt. % | 99.6 |

EXAMPLE 2

A portion of a zeolite produced in accordance with Example 1 was calcined in a muffle furnace at 1000° F. for three hours, sized to 30-60 mesh, and 2.5 g (4.8 cc) were charged to a 5/16" ID stainless steel microreactor. The ZSM-5 was treated in situ with hydrogen at 900° F. for one hour. Propylene, admixed with 50 volume percent of hydrogen, was then passed over the catalyst at 500 psig (total pressure—1000 psig), 0.4 WHSV, 400° F. for two hours. No C$_6$+ liquid product was obtained.

EXAMPLE 3

Conversion of Propylene over a physical mixture of 50 ppm Al$_2$O$_3$ ZSM-5 and alumina A mixture of 1.63 g (2.9 cc) 50 ppm Al$_2$O$_3$ ZSM-5 plus 0.87 g (1.8 cc) alpha alumina monohydrate, both sized to 30–60 mesh and calcined at 1000° F. for three hours, was charged to the reactor and treated again in situ with hydrogen at 1000° F. for one hour. Propylene was then passed over the catalyst under the same conditions as in Example 2 for successive periods of 16 ½ and 22½ hours. Again, no C$_6$+liquid was formed.

EXAMPLE 4

Preparation of 50 ppm Al$_2$O$_3$ ZSM-5 with 35 wt. % alumina binder

The 50 ppm Al$_2$O$_3$ ZSM-5, as synthesized, was mulled with 35 wt. % alpha alumina monohydrate with added deionized water, extruded (1/16") at 25 t/in$^2$ pressure, dired at 230° F., precalcined in ammonia for three hours at 1000° F., ammonium exchanged to insure sodium content less than 0.02 wt. %, dried at 230° F., and calcined in air for three hours at 1000° F.

EXAMPLE 5

Propylene Over 50 ppm Al$_2$O$_3$ with 35 wt. % alumina binder

A 2.50 g quantity of the product from Example 4, sized to 30–60 mesh, was charged to the reactor, treated with hydrogen in situ for one hour at 900° F. Then propylene was passed over the catalyst under the conditions of Examples 2 and 3. Results are shown below:

|  | Yields | |
|---|---|---|
| Material Balance Time, | 19½ | 22 |
| Hrs. | | |
| Time on Stream, Days | 0.8 | 0.9 |
| Yields, wt. % | | |
| C$_1$ + C$_2$ | <0.1 | <0.1 |
| C$_3$= | 22.7 | 22.7 |
| C$_3$ | 2.4 | 3.0 |
| C$_4$'s | 1.2 | 1.4 |
| C$_5$'s | 1.8 | 1.4 |
| C$_6$+ | 71.9 | 71.4 |
| | 100.0 | 100.0 |

The C$_6$+liquid from the two runs was composited and distilled to give 28.6 wt. % 330° F.−gasoline and 42.9 wt. % 330° F.+ fuel oil. The gasoline had an octane number (R+O) of 94 and the fuel oil a pour point of less than −70° F., diesel index 67.

| 330° F.− Gasoline | |
|---|---|
| Yield, wt. % | 28.6 |
| Gravity, °API | 64.7 |
| Gravity, specific | 0.7213 |
| O.N., R + O | 94 |
| Boiling Range, °F. | |
| 5% | 132 |
| 50% | 267 |
| 95% | 328 |
| 330° F.+ Distillate (Fuel Oil) | |
| Yield, wt. % | 42.9 |
| Gravity, °API | 42.7 |
| Gravity, specific | 0.8123 |
| Pour Point, °F. | <−75 |
| Aniline No. | 157.2 |
| Diesel Index | 67 |
| Hydrogen, wt. % | 13.93 |
| Carbon | 86.15 |
| H/C Ratio | 1.92 |
| Boiling Range, °F. | |
| 5% | 339 |
| 50% | 458 |
| 95% | 651 |

EXAMPLE 6

Waxy Lube Raffinate Charge

A furfural extracted, waxy heavy neutral lube stock, designated Coryton 0048 raffinate, was processed over the catalysts of Examples 1 and 4 at 1 LHSV, 400 psig, 2500 SCF hydrogen/bbl. Results are compared below with a conventional ZSM-5 catalyst having an Alpha Value of 70.

| | Lube Dewaxing | | |
|---|---|---|---|
| Catalyst | Mixture* Example 1 + Al$_2$O$_3$ | Example 4 | Conventional Catalyst |
| Temperature, °F. | 650 | 651 | 551 |
| Material Balance Time, Hrs. | CHARGE | 18½ | 18 |
| Yields, wt. % | | | |
| C$_1$ + C$_2$ | LIQUID | <0.1 | 0.1 |
| C$_3$ | PRODUCT | 0.9 | 2.2 |
| C$_4$ | | 2.5 | 3.8 |
| C$_5$ | | 1.8 | 2.1 |
| C$_6$-650° F. | | 9.4 | 8.8 |
| 650° F.+ Lube | | 85.1 | 82.8 |
| 650° F. Lube Properties | | | |
| Gravity, °API | 29.1 | 28.4 | 28.5 |
| Gravity, specific | 0.8811 | 0.8849 | 0.8844 |
| Pour Point, °F. | >115 | >115 | +20 | +10 |
| KV @ 40° C., cs | — | — | 95.08 | 109.0 |
| KV @ 100° C., cs | 9.91 | — | 10.77 | 11.42 |
| V.I. | — | — | 96.3 | 90.0 |

*Physical mixture of 1.7 g (3.0 cc) Example 1 plus 0.9 g (1.8 cc) alumina.

The 50 ppm Al$_2$O$_3$ catalyst had essentially no lube catalytic dewaxing activity. Addition of the alumina binder (Example 4) imparts activity with no adverse effect on the ZSM-5 shape selectivity as indicated by the pour point-viscosity index relationship. In this example it is less active but more selective than the standard conventional catalyst, i.e. gives a higher viscosity index at about the same pour point.

EXAMPLES 7–8

The following examples will illustrate that the use of zeolites having a significant amount of alumina, i.e. a silica/alumina mole ratio of 1600 or less, are not activated by the procedure of this invention, but rather, their activity is diluted.

EXAMPLE 7

70/1 $SiO_2/Al_2O_3$ ZSM-5 2.5 wt $Al_2O_3$, 25,000 ppm

Propylene was passed over the 70/1 $SiO_2/Al_2O_3$ ZSM-5 catalyst, with and without 35% alumina binder under the same conditions as those used in Examples 2, 3 and 5. Results are listed below:

| Catalyst | No Binder | 35% Alumina Binder |
|---|---|---|
| Temperature, °F. | 401 | 400 |
| WHSV | 0.6 | 0.4 |
| Material Balance Time, Hrs. | 17 | 22.5 |
| Yields, Wt. % | | |
| $C_1 + C_2$ | 0.1 | 0.1 |
| $C_3=$ | 1.2 | 2.0 |
| $C_3$ | 1.9 | 3.1 |
| $C_4$'s | 0.9 | 0.4 |
| $C_5$'s | 1.3 | 0.6 |
| $C_6+$ | 94.6 | 93.9 |
| | 100.0 | 100.0 |
| Liquid Product Boiling Range, °F. | | |
| 5% | 246 | 221 |
| 10% | 314 | 266 |
| 30% | 453 | 368 |
| 50% | 539 | 446 |
| 70% | 604 | 525 |
| 90% | 733 | 641 |
| 95% | 786 | 709 |

It can be seen that the catalyst without binder was actually more active than that with binder, i.e. the liquid product had a higher boiling range. The binder in this case "dilutes" the concentration of ZSM-5 and thus decreases the activity of a given weight of final catalyst.

EXAMPLE 8

In this example a ZSM-5 having a silica-to-alumina ratio of 1600:1 (about 0.10 wt. % alumina, or 1,000 ppm) was used. The waxy lube raffinate of Example 6 was processed over this 600/1 $SiO_2/Al_2O_3$ ZSM-5, with and without 35% alumina binder. Conditions were again the same as those used in that example.

| Catalyst | No Binder* | 35% Alumina Binder |
|---|---|---|
| Temperature, °F. | 651 | 650 |
| Material Balance Time Hrs. | 19 | 18 |
| Yields, wt. % | | |
| $C_1 + C_2$ | <0.1 | 0.1 |
| $C_3$ | 1.6 | 2.1 |
| $C_4$ | 2.9 | 5.0 |
| $C_5$ | 1.8 | 2.7 |
| $C_6$-650° F. | 10.7 | 13.7 |
| 650° F.+ Lube | 82.5 | 76.2 |
| 650° F.+ Lube Properties | | |
| Gravity, °API | 27.4 | 27.1 |
| Specific | 0.8905 | 0.8922 |
| Pour Point, °F. | −20 | +10 |
| KV @ 40° C., cs | 113.9 | 109.1 |
| KV @ 100° C., cs | 11.44 | 11.21 |
| V.I. | 84.6 | 86.2 |

*Physical mixture of ZSM-5 plus alumina, alumina equal in weight to that present in bound catalyst From the above example, it can be seen that a binder is not necessary for generation of an active catalyst at this aluminal level, and in fact, the presence of alumina actually dilutes the activity of the catalyst without the binder.

EXAMPLE 9

The procedure of Example 4 was repeated with the sole exception that no water was used in mulling the alumina with a high silica ZSM-5.

EXAMPLE 10

In this example alumina alone was mulled with added water (no high silica zeolite) and then the high silica zeolite of Example 2 was wetted with the extract liquid and thereafter processed in identical manner to Example 2, i.e. ammonium precalcination for three hours at 1000°, base exchanged with an ammonium solution to reduce the sodium content to 0.02 wt. % followed by air calcination.

EXAMPLE 11

This example consisted of the use of 100% Kaiser alumina binder alone in order to completely eliminate the possibility that alumina itself was responsible for any catalytic activity.

The catalysts of Examples 9, 10 and 11 were evaluated for the conversion of propylene under conditions recited in Examples 2 and 3 and the results are shown in the following table together with results from some of the previously referred to examples.

TABLE

| | Conversion of Propylene | | | | | | |
|---|---|---|---|---|---|---|---|
| Example | Pure Crystals 2 | Physical Mixture With Binder 3 | Dry-Mulled With Binder 9 | Wetted With $H_2O$ Extract With Binder 10 | Wet-Mulled With Binder 4 | | Alumina alone 11 |
| WHSV, on total | 0.4 | 0.6 | 0.6 | 0.6 | 0.5 | 0.6 | 0.5 |
| Material Balance Time, Hrs. | 2 | 15 | 18 | 18 | 19.5 | 18.5 | 2 |
| $C_3 =$ Conversion, wt % | 16 | 15 | 16 | 5 | 77 | 77 | 55 |
| Yields, wt. % | | | | | | | |
| $C_1 + C_2$ | 0.1 | 0.5 | 0.1 | — | — | 0.3 | — |
| $C_3=$ | 84.0 | 85.5 | 83.6 | 95.2 | 22.7 | 22.6 | 45.4 |
| $C_3$ | 7.9 | 13.3 | 3.3 | 0.9 | 2.4 | 1.8 | 53.8 |
| $C_4 + C_5$ | 8.0 | 0.7 | 8.2 | 2.7 | 3.0 | 3.0 | 0.8 |
| $C_6+$ | 0.1 | 0.1 | 4.8 | 1.1 | 71.9 | 72.3 | — |
| | 100.0 | 100.0 | 100.0 | 100.0 | 100.0 | 100.0 | 100.0 |
| 330° F.+ Distillate | — | — | — | — | 56 | — | — |

TABLE-continued

| | | Conversion of Propylene | | | | |
|---|---|---|---|---|---|---|
| Example | Pure Crystals 2 | Physical Mixture With Binder 3 | Dry-Mulled With Binder 9 | Wetted With H$_2$O Extract With Binder 10 | Wet-Mulled With Binder 4 | Alumina alone 11 |
| % of Liq. Prod. | | | | | | |

From the above table, the pure crystals, i.e. Example 2 made no liquid product. The physical mixture, i.e. Example 3, eliminated the possibility that the high silica ZSM-5 and the alumina particles as such are interacting and the dry mulling experiment, i.e. Example 9, eliminates ammonium exchange in the final calcination as being involved in the generation of active sites. The water extract experiment, i.e. Example 10, eliminates room temperature wet mulling as a possible source of dissolved alumina entering the ZSM-5 pores. The alumina only experiment, i.e. Example 11, also made no liquid product and as such this result confirms the fact that the binder as such in the wet mulled catalyst is not making liquid product at 400° F.

EXAMPLES 12-14

Another series of examples were carried out in order to illustrate the criticality of the use of water during the mulling of the high silica zeolite with the alumina. In all of these examples, 65 wt. % of the ultra low alumina zeolite of Example 1 was used and the binder was 35 wt. % alpha alumina monohydrate. Each sample was treated after forming in accordance with the procedure of Example 4. Examples 12 and 14 did not use water. Example 13 did use water but no hydraulic pressure.

The compositions were evaluated together for Alpha activity.

As is known in the art, the Alpha Value is an approximate indication of the catalytic cracking activity of the catalyst compared to a standard catalyst and it gives the relative rate constant (rate of normal hexane conversion per volume of catalyst per unit time). The Alpha test is described in U.S. Pat. No. 3,354,078 and in The Journal of Catalysis, Vol. IV, pp. 522-529 (August 1965), each incorporated herein by reference as to that description.

The results are shown in the following table along with a comparison with the catalyst of Example 4.

TABLE

| Example | 12 | 13 | 14 | 4 |
|---|---|---|---|---|
| Method of Incorporation | Dry Mulling[1] and Hand Pressing | Wet Mulling[1] and Hand Pressing | Dry Mixing[2] and Hand Pressing | Wet Mulling[1] Hydraulic Extrusion (at 25 ton pressure[3]) |
| Alpha Activity | 0.25 | 1.0 | 0.13 | 5.7 |

[1]Mulling - Mix in a muller (Cincinnati Muller Co.) for 10-15 minutes with or without water
[2]Mixing - Mechanical mixing with no kneading action
[3]Extrusion - Extrusion using a hydraulic RAM extruder As can be seen, the preparation without water, i.e. Examples 12 and 14, resulted in very low Alpha Values—even though the ammonia precalcination, ammonium exchange and air calcination were carried out. However, the preparations with water gave enhanced results.

EXAMPLES 15-16

Examples 15 and 16 illustrate the effect of time and temperature of ammonia precalcination on alpha activity and a comparison is made with the catalyst of Example 4. In each of Examples 15 and 16, the procedure of Example 4 was followed.

The results and operation conditions are shown in the following table.

TABLE

| Example | 15 | 4 | 16 |
|---|---|---|---|
| Precalcination | | | |
| Temperature, °F. | 800 | 1000 | 1200 |
| Time, Hr. | 8 | 3 | 3 |
| Atmosphere | NH$_3$ | NH$_3$ | NH$_3$ |
| Alpha Activity | 0.5 | 5.7 | 3.0 |

EXAMPLES 17-18

Examples 17 and 18 show the effect of binder concentration on activation.

In each of Examples 17 and 18 the exact procedure of Example 4 was followed with the exception of varying the binder content. Note that the binder has a surprising effect on activity.

The results and specific formualtions are shown below together with the catalyst of Example 4.

TABLE

| Example | 17 | 4 | 18 |
|---|---|---|---|
| Zeolite/Binder (wt. basis) | 90/10 | 65/35 | 10/90 |
| Alpha activity | 0.40 | 5.7 | 3.0 |
| Alpha activity, Normalized* | 0.24 | 5.7 | 19.5 |

*Normalized to unit weight of zeolite based on 65/35 wt. ratio.

EXAMPLES 19-22

These examples show that ZrO$_2$ and TiO$_2$ as binder material impart significant Alpha activity compared to Al$_2$O$_3$, using mortar and pestle mixing and pressing as the method of incorporation (insufficient material for hydraulic extrusion). SiO$_2$ as a binder has essentially no effect on Alpha activity.

Details of the preparation of these materials are described below.

EXAMPLE 19

Zirconia Binder

As synthesized ultra low Al ZSM-5 zeolite was intimately mixed with a zirconia gel of 25% solution by weight (from duPont Chemical). The weight ratio of ZSM-5 to ZrO$_2$ was adjusted to 65/35. The mixture was then dried and calcined in a NH$_3$ stream at 1000° F. for three hours. The Na content in the material was then exchanged with 1 N NH$_4$/NO$_3$ solution to reduce to less than 0.05%. The sample was then sized to 14/25 mesh size material and calcined to 1000° F. in air for three hours.

EXAMPLE 20

Titania Binder

Preparation procedure and catalytic test method of the catalyst are similar to that in Example 19 except that 25% titania gel (from duPont Chemical) was used instead of ZrO$_2$ gel.

EXAMPLE 21

Silica Binder

Preparation procedure and catalytic test method of the catalyst are similar to that in Example 19 except that 30% colloidal SiO$_2$ (from duPont Chemical) was used instead of ZrO$_2$ gel.

EXAMPLE 22

Alumina Binder

Same as Example 19, except Kaiser alpha alumina monohydrate was used.

The results are shown in the following table together with the results obtained with the composition of Example 1.

TABLE

| Example | 19 | 20 | 21 | 22 | 1 |
|---|---|---|---|---|---|
| Binder Material | ZrO$_2$ | TiO$_2$ | SiO$_2$ | Al$_2$O$_3$ | None |
| Zeolite/Binder (wt. basis) | ← 65/35 → | | | | Pure Zeolite |
| Method of Incorporation | Mortar and Pestle Mix and Hand Pressing | | | | |
| Alpha Activity | 0.72 | 0.77 | 0.28 | 0.51 | 0.2 |

EXAMPLES 23-25

These examples illustrate that the mesh size of the catalyst is not critical.

In each of Examples 23-25, the catalyst prepared by the process of Example 4 was ground to different mesh size and the Alpha activity measured.

The results are shown in the following table.

TABLE

| Example | 23 | 24 | 25 |
|---|---|---|---|
| Mesh Size of Catalyst | 12-14 | 14-25 | 25-40 |
| Alpha Activity | 5.8 | 5.7 | 5.2 |

What is claimed is:

1. A process for cracking a feedstock comprising paraffin hydrocarbon compounds to lower molecular weight hydrocarbon compounds, which process comprises contacting said feedstock at cracking conditions with a catalyst composition prepared by a method for enhancing the acid activity of a high silica-containing crystalline zeolite containing from about 50 ppm to less than about 1000 ppm alumina and having an alpha value of less than about 5, which method comprises the steps of:
   (1) mulling said zeolite with an inorganic oxide binder selected from the group consisting of alumina, zirconia, titania and mixtures thereof in the presence of water,
   (2) forming or shaping the composition of step (1) at a pressure of from about 2 to about 50 tons per square inch,
   (3) calcining the formed or shaped composition of step (2) in a non-oxidizing atmosphere at from about 900° F. to about 1200° F. for from about 1 hour to about 5 hours,
   (4) treating said calcined composition from step (3) by base exchange if the sodium content thereof is greater than about 0.02 wt. % in order to reduce the sodium content thereof to less than about 0.02 wt. %, and, if treated,
   (5) calcining said treated composition of step (4) at elevated temperature.

2. The process of claim 1 wherein the composition of method step (1) comprises from about 20 to about 95 wt. % inorganic oxide binder.

3. The process of claim 1 wherein method step (2) is carried out at a pressure greater than 5 tons per square inch.

4. The process of claim 1 in which the zeolite has the structure of ZSM-5, ZSM-5/ZSM-11 intermediate or ZSM-11.

5. The process of claim 4 in which the zeolite has the structure of ZSM-5.

6. The process of claim 1 wherein the non-oxidizing atmosphere of method step (3) comprises ammonia.

7. The process of claim 1 wherein said cracking conditions include a temperature of from about 230° C. to about 800° C., a pressure of from about 0.1 atmosphere to about 35 atmospheres and a liquid hourly space velocity of from about 0.6 hr$^{-1}$ to about 10 hr$^{-1}$.

8. A process for catalytically dewaxing a wax-containing oil feed to provide a catalytically dewaxed oil with reduced pour point, which process comprises contacting said feed at a temperature of from about 230° C. to about 500° C., a pressure of from about 0.1 atmosphere to about 200 atmospheres and a weight hourly space velocity of from about 0.08 hr$^{-1}$ to about 2000 hr$^{-1}$ with a catalyst composition prepared by a method enhancing the acid activity of a high silica-containing crystalline zeolite containing from about 50 ppm to less than about 1000 ppm alumina and having the structure of ZSM-5, ZSM-5/ZSM-11 intermediate or ZSM-11, which method comprises the steps of:
   (1) mulling said zeolite with an inorganic oxide binder selected from the group consisting of alumina, zirconia, titania and mixtures thereof in the presence of water,
   (2) forming or shaping the composition of step (1) at a pressure of from about 2 to about 50 tons per square inch,
   (3) calcining the formed or shaped composition of step (2) in a non-oxidizing atmosphere at from about 900° F. to about 1200° F. for from about 1 hour to about 5 hours,
   (4) treating said calcined composition from step (3) by base exchange if the sodium content thereof is greater than about 0.02 wt. % in order to reduce the sodium content thereof to less than about 0.02 wt. %, and, if treated,
   (5) calcining said treated composition of step (4) at elevated temperature.

9. The process of claim 8 wherein the composition of method step (1) comprises from about 20 to about 95 wt. % inorganic oxide binder.

10. The process of claim 8 wherein method step (2) is carried out at a pressure greater than 5 tons per square inch.

11. The process of claim 8 in which the zeolite has the structure of ZSM-5.

12. The process of claim 8 wherein the non-oxidizing atmosphere of method step (3) comprises ammonia.

13. A process for catalytically dewaxing a wax-containing lubricating oil base stock to provide a lubricating oil stock with reduced pour point, which process comprises contacting said base stock at a temperature of from about 230° C. to about 500° C., a pressure of from about 0.1 atmosphere to about 200 atmospheres, a weight hourly space velocity of from about 0.08 hr$^{-1}$ to about 2000 hr$^{-1}$ and a hydrogen/oil mole ratio of 0 to about 100 with a catalyst composition prepared by a method for enhancing the acid activity of a high silica-containing crystalline zeolite containing from about 50 ppm to less than about 1000 ppm alumina and having an alpha value of less than about 5, said zeolite having the structure of ZSM-5, ZSM-5/ZSM-11 intermediate, or ZSM-11, which method comprises the steps of:

(1) mulling said zeolite with an inorganic oxide binder selected from the group consisting of alumina, zirconia, titania and mixtures thereof in the presence of water, (2) forming or shaping the composition of step (1) at a pressure of from about 2 to about 50 tons per square inch, (3) calcining the formed or shaped composition of step (2) in a non-oxidizing atmosphere at from about 900° F. to about 1200° F. for from about 1 hour to about 5 hours, (4) treating said calcined composition from step (3) by base exchange if the sodium content thereof is greater than about 0.02 wt. % in order to reduce the sodium content thereof to less than about 0.02 wt. %, and, if treated, (5) calcining said treated composition of step (4) at elevated temperature.

14. The process of claim 13 wherein the composition of method step (1) comprises from about 20 to about 95 wt. % inorganic oxide binder.

15. The process of claim 13 wherein method step (2) is carried out at a pressure greater than 5 tons per square inch.

16. The process of claim 13 in which the zeolite has the structure of ZSM-5.

17. The process of claim 13 wherein the non-oxidizing atmosphere of method step (3) comprises ammonia.

* * * * *

UNITED STATES PATENT AND TRADEMARK OFFICE
CERTIFICATE OF CORRECTION

PATENT NO. : 4,719,004

DATED : January 12, 1988

INVENTOR(S) : Pochen Chu et al

It is certified that error appears in the above-identified patent and that said Letters Patent is hereby corrected as shown below:

Col. 1, line 10, "563,435" should be --4,563,435--
Col. 4, line 44, "n order" should be --in order--
Col. 9, line 47, "600" should be --1600--

Signed and Sealed this

Thirty-first Day of May, 1988

Attest:

DONALD J. QUIGG

Attesting Officer

Commissioner of Patents and Trademarks